(12) United States Patent
Fraley et al.

(10) Patent No.: US 6,622,046 B2
(45) Date of Patent: Sep. 16, 2003

(54) SUBCUTANEOUS SENSING FEEDTHROUGH/ELECTRODE ASSEMBLY

(75) Inventors: Mary A. Fraley, Minnetonka, MN (US); Ronald F. Hoch, Andover, MN (US); George Johnstone, Brooklyn Center, MN (US); Joseph F. Lessar, Coon Rapids, MN (US); Lynn M. Seifried, Minneapolis, MN (US); James Strom, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 174 days.

(21) Appl. No.: 09/850,331

(22) Filed: May 7, 2001

(65) Prior Publication Data

US 2002/0165588 A1 Nov. 7, 2002

(51) Int. Cl.[7] .............................. A61N 1/05; A61N 1/375
(52) U.S. Cl. .............................. 607/36; 607/37
(58) Field of Search ........................... 607/36, 37

(56) References Cited

U.S. PATENT DOCUMENTS

| | | | |
|---|---|---|---|
| 3,983,867 A | 10/1976 | Case | 128/2.06 G |
| 4,023,565 A | 5/1977 | Ohlsson | 128/2.06 B |
| 4,082,086 A | 4/1978 | Page et al. | 128/2.06 E |
| 4,121,576 A | 10/1978 | Greensite | 128/2.06 V |
| 4,170,227 A | 10/1979 | Feldman et al. | 128/704 |
| 4,263,919 A | 4/1981 | Levin | 128/708 |
| 4,310,000 A | 1/1982 | Lindemans | 128/419 PG |
| 4,313,443 A | 2/1982 | Frosch et al. | 128/642 |
| 4,476,868 A | 10/1984 | Thompson | 128/419 PG |
| 4,593,702 A | 6/1986 | Kepski et al. | 128/696 |
| 4,674,508 A | 6/1987 | DeCote | 128/419 PT |
| 4,729,376 A | 3/1988 | DeCote, Jr. | 128/419 PT |
| 5,052,388 A | 10/1991 | Sivula et al. | 128/419 PG |
| 5,331,966 A | 7/1994 | Bennett et al. | 128/696 |
| 5,345,362 A | 9/1994 | Winkler | 361/681 |
| 5,372,605 A | 12/1994 | Adams et al. | 607/5 |
| 5,431,695 A * | 7/1995 | Wiklund et al. | 607/36 |
| 5,614,331 A | 3/1997 | Takeuchi et al. | 429/9 |
| 5,650,759 A * | 7/1997 | Hittman et al. | 607/37 |
| 5,735,884 A * | 4/1998 | Thompson et al. | 607/36 |
| 5,782,891 A * | 7/1998 | Hassler et al. | 607/36 |
| 6,044,295 A | 3/2000 | Pilz et al. | 607/4 |
| 6,052,623 A * | 4/2000 | Fenner et al. | 607/36 |
| 6,087,809 A | 7/2000 | Gan et al. | 320/135 |
| 6,498,951 B1 * | 12/2002 | Larson et al. | 607/36 |

FOREIGN PATENT DOCUMENTS

WO     WO 99/05750     2/1999     .......... H01M/16/00

* cited by examiner

Primary Examiner—Carl Layno
(74) Attorney, Agent, or Firm—Girma Wolde-Michael

(57) ABSTRACT

Structures and methods relating to electrodes for incorporation into a feedthrough with a profile adapted for subcutaneous sensing of physiologic and cardiac signals. Electrode assemblies are adapted for integration with feedthrough to enable maximal electrode spacing, minimal myopotential electrical noise and provide reliable insulation from the IMD housing. Various structures and manufacturing processes are implemented to provide a large sensing surface with a low profile. The subcutaneous sensing electrode assembly provides a leadless sensing system and further enhances installation and follow-up procedures.

38 Claims, 12 Drawing Sheets

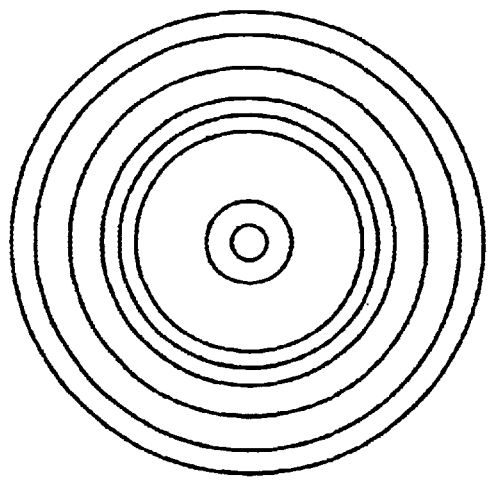
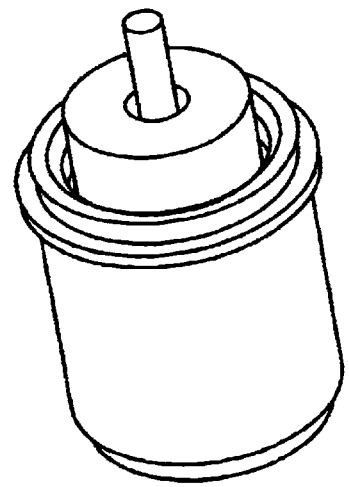
FIG. 6B
FIG. 6C
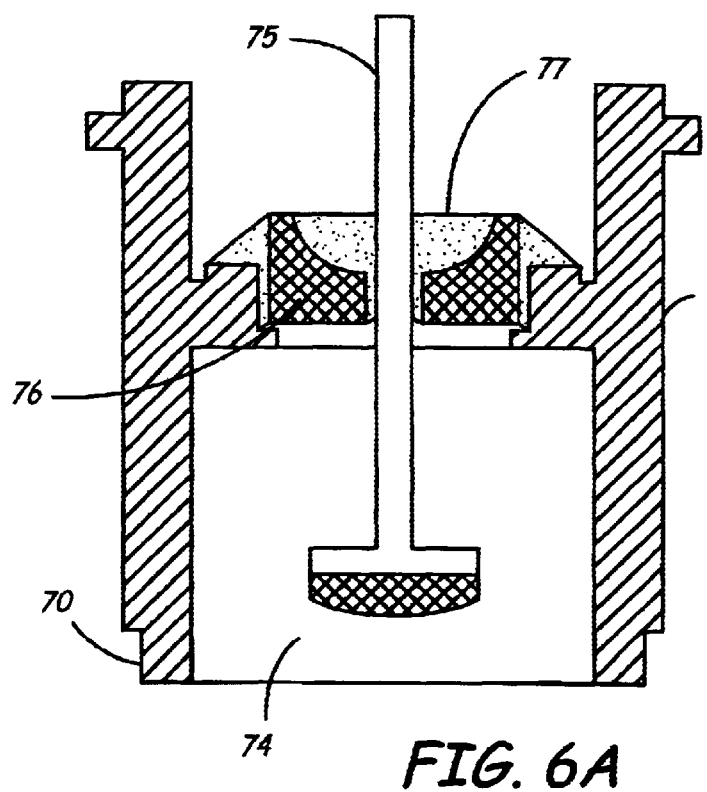
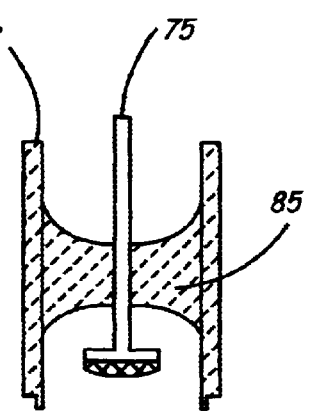
FIG. 6A
FIG. 6D

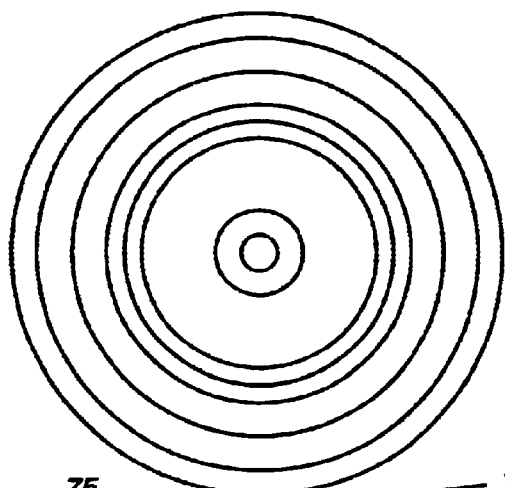
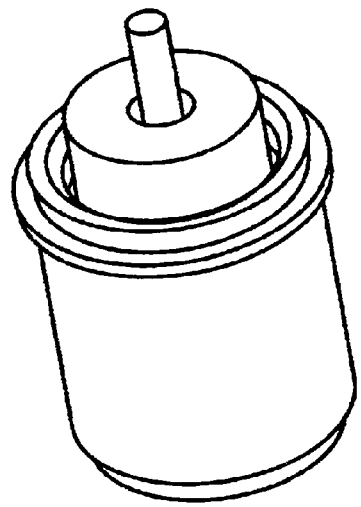
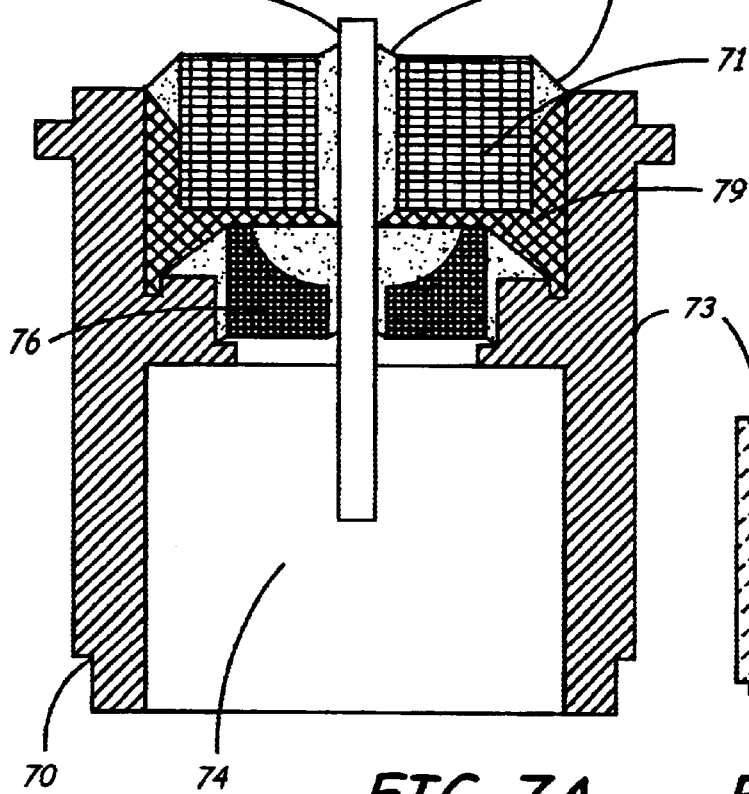
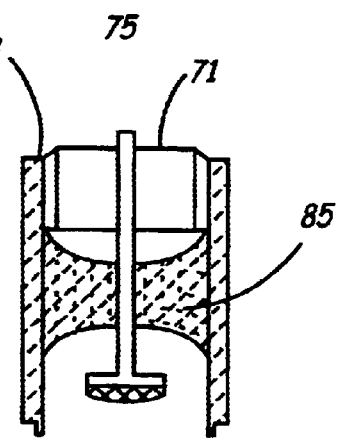
FIG. 7B
FIG. 7C
FIG. 7A
FIG. 7D

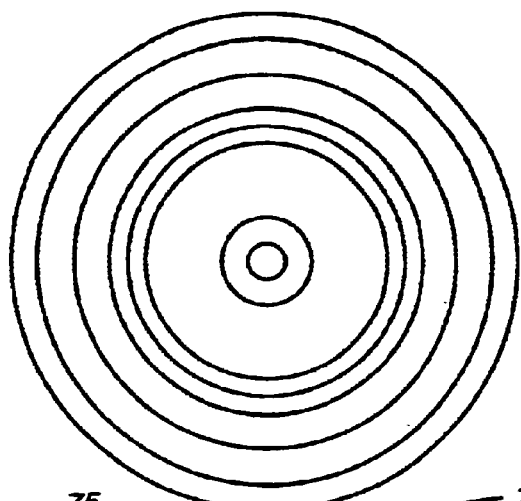
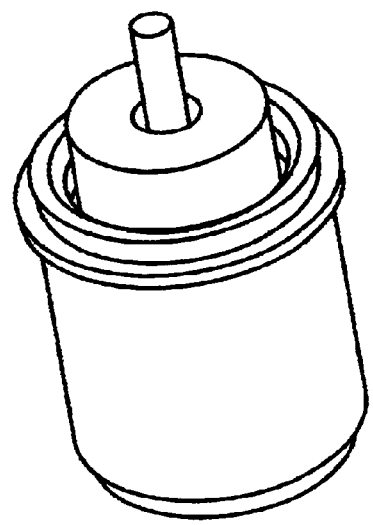
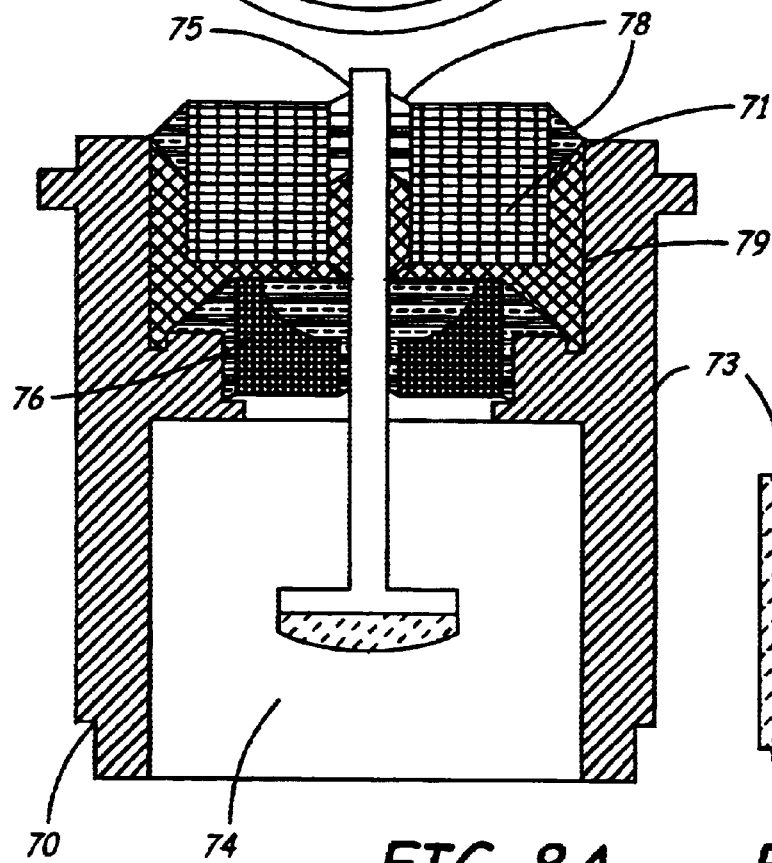
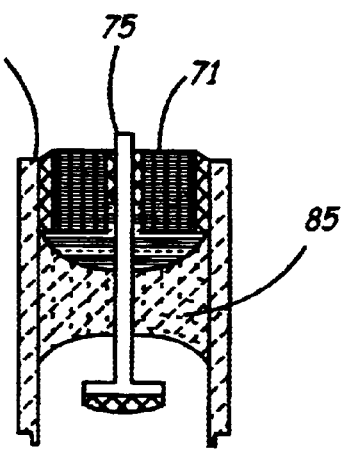
FIG. 8B
FIG. 8C
FIG. 8A
FIG. 8D

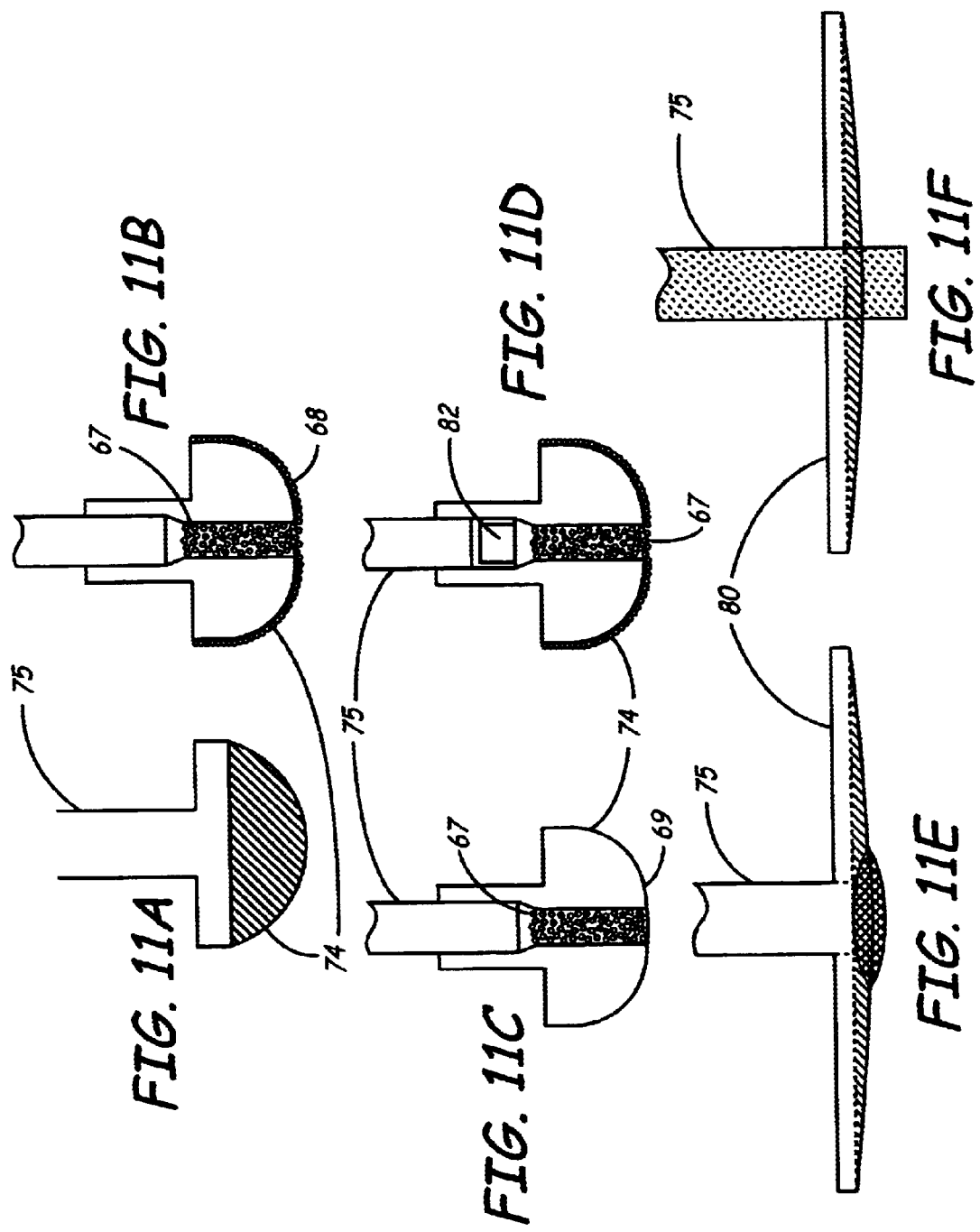

SUBCUTANEOUS SENSING FEEDTHROUGH/ELECTRODE ASSEMBLY

FIELD OF THE INVENTION

The present invention relates generally to implantable pacemakers and more particularly to subcutaneous electrodes implemented to sense, acquire, and store electrocardiographic data and waveform tracings from an implanted pacemaker. More particularly, the present invention relates to various embodiments including the manufacture and assembly of such electrodes with feedthroughs that facilitate their electrical connection to a pacemaker's circuitry.

BACKGROUND OF THE INVENTION

Electrocardiogram (ECG) signals are commonly used in medicine to determine the status of the electrical conduction system of the human heart. As practiced, an ECG recording device is commonly attached to the patient via ECG leads connected to skin electrodes arrayed on the patient's body so as to achieve a recording that displays the cardiac waveforms in any one of 12 possible vectors.

Since the implantation of the first cardiac pacemaker, implantable IMD technology has advanced with the development of sophisticated, programmable cardiac pacemakers and pacemaker-cardioverter-defibrillator (PCD) arrhythmia control devices designed to detect arrhythmias and dispense appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) and the electrogram (EGM). The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. Acquisition and use of ECG tracing(s), on the other hand, has generally been limited to the use of an external ECG recording machine attached to the patient via surface electrodes of one sort or another.

The aforementioned ECG systems that use detection and analysis of the PQRST complex are all dependent upon the spatial orientation and number of externally applied electrodes available near or around the heart to detect or sense the cardiac depolarization wave front.

As the functional sophistication and complexity of implantable medical device systems increased over the years, it has become necessary for such systems to include communication means between implanted devices and/or an external device, for example, a programming console, monitoring system, and similar systems. For diagnostic purposes, it is desirable that the implanted device be able to communicate information regarding the device's operational status and the patient's condition to the physician or clinician. State of the art implantable devices are available which can transmit or telemeter a digitized electrical signal to display electrical cardiac activity (e.g., an ECG, EGM, or the like) for storage and/or analysis by an external device.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. In spite of these advances in the medical device art, the surface ECG has remained a standard diagnostic tool since the very beginning of pacing and remains so today. The twelve-lead electrocardiogram (ECG) is generally the first procedure used to determine cardiac status prior to implanting a pacing system. Thereafter, the physician will typically use an ECG available through the programmer or extra corporeal telemetry transmission to check the pacemaker's efficacy after implantation. Previous ECG tracings are placed into the patient's records for later use in comparing against more recent tracings. It must be noted, however, that current art practice in ECG recording (whether through a direct connection to an ECG recording device or to a pacemaker programmer), involves the use of external ECG electrodes and leads.

Unfortunately, surface ECG electrodes have technical drawbacks. For example, electrocardiogram analysis performed using existing external or body surface ECG systems can be limited by mechanical problems and poor signal quality. Electrodes attached externally to the body are a major source of signal quality problems and errors because of susceptibility to interference such as muscle noise, electromagnetic interference, high frequency communication equipment interference, and baseline shift from respiration, for example. Signal degradation also occurs due to contact problems, ECG waveform artifacts, and patient discomfort. Externally attached electrodes are also subject to motion artifacts from positional changes and the relative displacement between the skin and the electrodes. Furthermore, external electrodes require special skin preparation, for example, application of electrolyte ointment or cream, to ensure adequate electrical contact. Such preparation, along with positioning the electrode and attachment of the ECG lead to the electrode needlessly prolongs the pacemaker follow-up session. One possible approach is to equip the implanted pacemaker with features for detecting cardiac signals and transforming them into a tracing that is the same as or comparable to tracings obtainable via ECG leads attached to surface (skin) electrodes.

Monitoring electrical activity of the human heart for diagnostic and related medical purposes is well known in the art. For example, U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems that combine surface EKG signals for artifact rejection.

The primary application of multiple electrode systems in the prior art appears to be vector cardiography from ECG signals taken from multiple chest and limb electrodes. This is a technique for monitoring the direction of depolarization of the heart including the amplitude of the cardiac depolarization waves. U.S. Pat. No. 4,121,576 issued to Greensite discloses such a system.

Numerous body surface ECG monitoring electrode systems have been implemented in the past to detect the ECG and conduct vector cardiographic studies. For example, U.S. Pat. No. 4,082,086 issued to Page, et al., discloses a four electrode orthogonal array that may be applied to the patient's skin both for convenience and to ensure precise orientation of one electrode with respect to the other. U.S.

Pat. No. 3,983,867 issued to Case describes a vector cardiography system employing ECG electrodes disposed on the patient in commonly used locations and a hex axial reference system orthogonal display for displaying ECG signals of voltage versus time generated across sampled bipolar electrode pairs.

U.S. Pat. No. 4,310,000 to Lindemans and U.S. Pat. Nos. 4,729,376 and 4,674,508 to DeCote, incorporated herein by reference, disclose the use of a separate passive sensing reference electrode mounted on the pacemaker connector block or otherwise insulated from the pacemaker case. The passive electrode is implemented to provide a sensing reference electrode that is not part of the stimulation reference electrode and thus does not carry residual after-potentials at its surface following delivery of a stimulation pulse.

Moreover, in regard to subcutaneously implanted EGM electrodes, the aforementioned Lindemans U.S. Pat. No. 4,310,000 discloses one or more reference sensing electrodes positioned on the surface of the pacemaker case as described above. In a related art, U.S. Pat. No. 4,313,443 issued to Lund describes a subcutaneously implanted electrode or electrodes for use in monitoring ECG.

U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

More recently, P-9033 Surround Shroud Connector and Electrode Housings for a Subcutaneous Electrode Array and Leadless ECGs, by Ceballos, et al. filed on Oct. 26, 2000, Ser. No. 09/697,438, incorporated herein by reference in its totality, discloses an alternate method and apparatus for detecting electrical cardiac signals via an array of subcutaneous electrodes located on a shroud circumferentially placed on the perimeter of an implanted pacemaker. An associated submission, P-9041 Subcutaneous Electrode for Sensing Electrical Signals of the Heart by Brabec et al, filed on Oct. 31, 2000, Ser. No. 09/703,152, incorporated herein by reference in its totality, discloses the use of a spiral electrode implemented in conjunction with the shroud described in P-9033. In addition, P-8786 Multilayer Ceramic Electrodes for Sensing Cardiac Depolarization Signals, filed Oct. 25, 2000, Ser. No. 09/696,365 and P-8787 Thin Film Electrodes for Sensing Cardiac Depolarization Signals, filed on Dec. 13, 2000, Ser. No. 09/736,046 both by Guck et al, incorporated herein by reference in their totality, disclose the use of multi-layer ceramic and thin film ECG electrodes placed into recesses incorporated along and into the peripheral edge of the implantable pacemaker.

SUMMARY OF THE INVENTION

The present invention relates to various electrode designs that allow direct incorporation of the electrode into a feedthrough. Depending on the design, the feedthrough ferrules may be welded individually into desired positions around the perimeter of an implantable pacemaker and then the feedthrough/electrodes fabricated into the existing ferrules. Alternatively, the complete feedthrough/electrode assembly may be fabricated and then welded as one body into the pacemaker. These feedthrough/electrode assemblies are electrically connected to the circuitry of an implantable pacemaker to create a leadless Subcutaneous Electrode Array (SEA) for the purpose of detecting cardiac depolarization waveforms displayable as electrocardiographic tracings on an external device in communication with the pacemaker. When the programming head of a programmer is positioned above an implanted device equipped with a leadless SEA electrocardiographic tracing waveforms may be displayed and viewed on the programmer screen. These waveforms may also be telemetered extra-corporeally to an external device located nearby or at some distance from the patient, as is described in P-7683, Leadless Fully Automatic Pacemaker Follow-Up by Combs and Berg, filed on Dec. 27, 2000, Ser. No. 09/749,169 incorporated herein by reference in its entirety.

The present invention, inter alia, may be a replacement for externally mounted electrodes and electrode wires in the prior art currently used on the leadless ECG implantable pacemaker, as described in U.S. Pat. No. 5,331,966 issued to Bennett. Typically, prior art practice includes electrodes placed on the face of the implanted pacemaker. When facing muscle, the electrodes are apt to detect myopotentials and are susceptible to baseline drift. The present invention minimizes myopotential detection and thereby makes the pacemaker less sensitive to orientation in the incision pocket of a patient. Further, allowing the device to be implanted on either side of the chest provides maximum electrode separation and minimal signal variation. This is primarily because of variations in pacemaker orientations within the pocket. Implantable device electrodes need to be placed on the perimeter of the pacemaker in such a way as to maximize the distance between electrode pairs.

The present invention eliminates the need for a compliant shroud that typically houses the surface mounted electrodes and connecting wires as described in patent application No. P-9033, "Surround Shroud Connector And Electrode Housings For A Subcutaneous Electrode Array And Leadless ECGs," by Ceballos et al. filed on Oct. 26, 2000, Ser. No. 09/697,438. Because the feedthrough/electrode assembly is an integral functional component, the complete assembly can be welded directly into the IPG casing. The present invention, including the manufacturing process disclosed herein eliminate the need for a compliant shroud in addition to structural efficiencies and ease of handling of the implantable pacemaker during the implant procedure.

The spacing of the electrodes in the present invention provides maximal electrode spacing, minimal myopotential electrical noise, and, at the same time, appropriate insulation from the pacemaker casing particularly because of the welding of the assemblies to the pacemaker casing. The electrode spacing around the pacemaker's perimeter preferably maintains a maximum and equal distance between the electrode pairs. Spacing arrangements such as disclosed with the three-electrode equal spacing embodiment maintain a maximum average signal. The arrangement is preferred because the spacing of the three vectors between the electrode pairs is equal and the angle between the vectors is equilateral, as is shown using mathematical modeling. Such an arrangement of electrode pairs also minimizes signal variation. An alternate three-electrode embodiment includes electrodes arranged so that the spacing of two vectors is equal and with angle between them set at 90°. Vectors in these embodiments can be combined to provide adequate sensing of cardiac signals (ECGs). Further disclosure of the position of three and four-electrodes in the Subcutaneous Electrode Array (SEA) may be found in P-8552, Subcutaneous Electrode Array Virtual ECG Lead by Panken and Reinke, filed on Nov. 22, 2000, Ser. No. 09/721,275, incorporated herein by reference in its entirety.

Similar to the use of a compliant shroud, helical electrode and multi-layer ceramic electrode, the present invention allows a physician or medical technician to perform leadless follow-up that, in turn, eliminates the time it takes to attach external leads to the patient. Such timesavings may significantly reduce the cost of follow-up, and may enable the physician or medical technician to see more patients. Other implementations include, but are not limited to: Holter monitoring with event storage, arrhythmia detection and monitoring, capture detection, ischemia detection and monitoring (S-T elevation and suppression on the ECG), changes in QT interval, and transtelephonic and telemetric monitoring.

BRIEF DESCRIPTION OF THE DRAWINGS

FIG. 6 shows four views of the second embodiment of the present invention that utilizes an ECG sensing electrode with a large surface area.

FIG. 7 shows four views of the third embodiment of the present invention that utilizes an ECG sensing electrode with a low profile and a filtered capacitor.

FIG. 8 shows four views of the fourth embodiment of the present invention that utilizes an ECG sensing electrode with a high surface area and a filtered capacitor.

FIG. 11 is a display of various electrode types that may be used in the assemblies shown in previous figures.

DETAILED DESCRIPTION OF THE DRAWINGS

Figure 1:
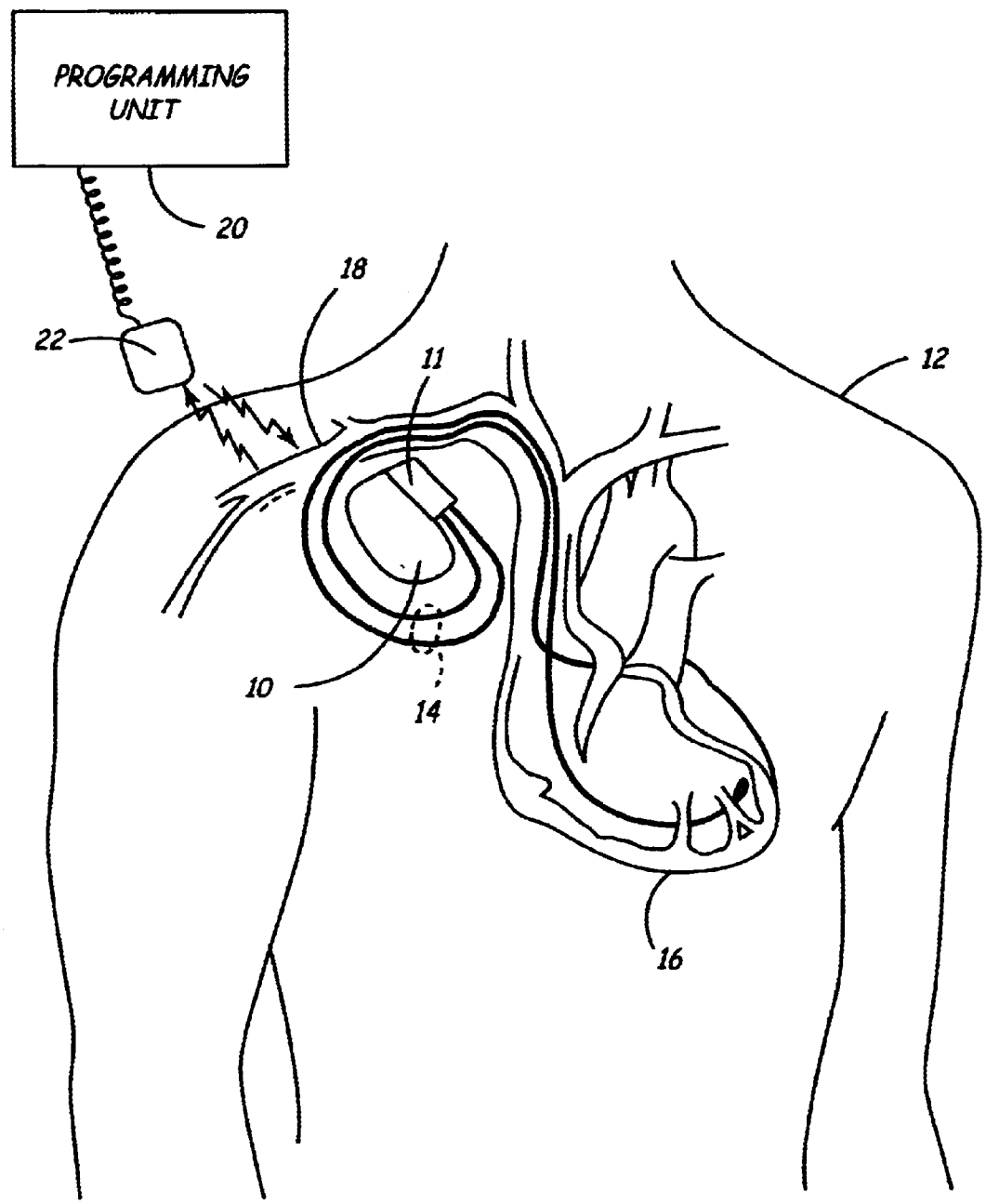
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes implantable device 10 that has been implanted in patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16.

Although the present invention will be described herein in an embodiment which includes a pacemaker, those of ordinary skill in the art having the benefit of the present disclosure will appreciate that the present invention may be practiced in connection with numerous other types of implantable medical device systems, and indeed in any application in which it is desirable to provide a communication link between two physically separated components.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
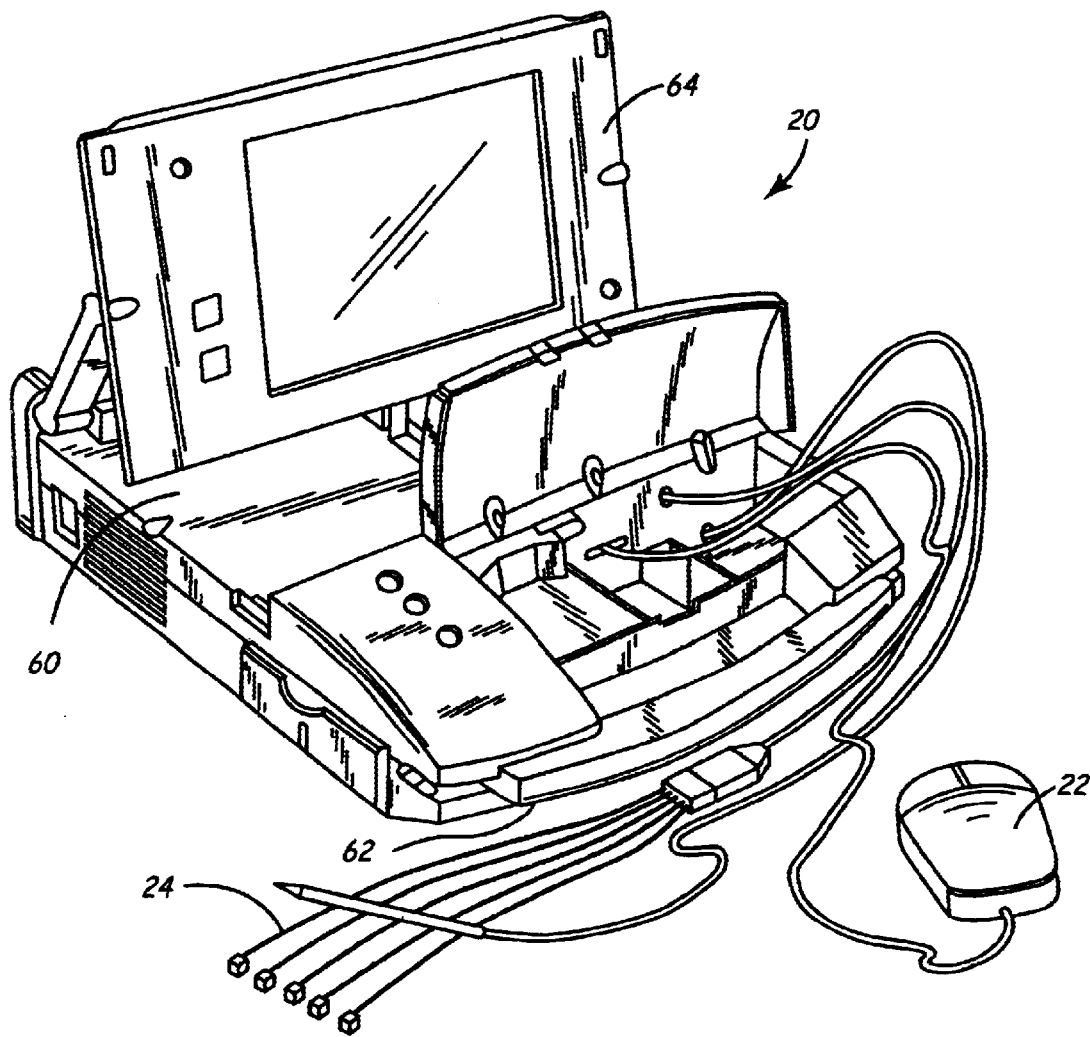
FIG. 2 is a perspective view of the external programming unit of FIG. 1.

FIG. 2 is a perspective view of programming unit 20 in accordance with the presently disclosed invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads 24. It is these leads that are rendered redundant by the present invention.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer. Programmer 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety; The Medtronic Model 9790 programmer is the implantable device-programming unit with which the present invention may be advantageously practiced.

Figure 3:
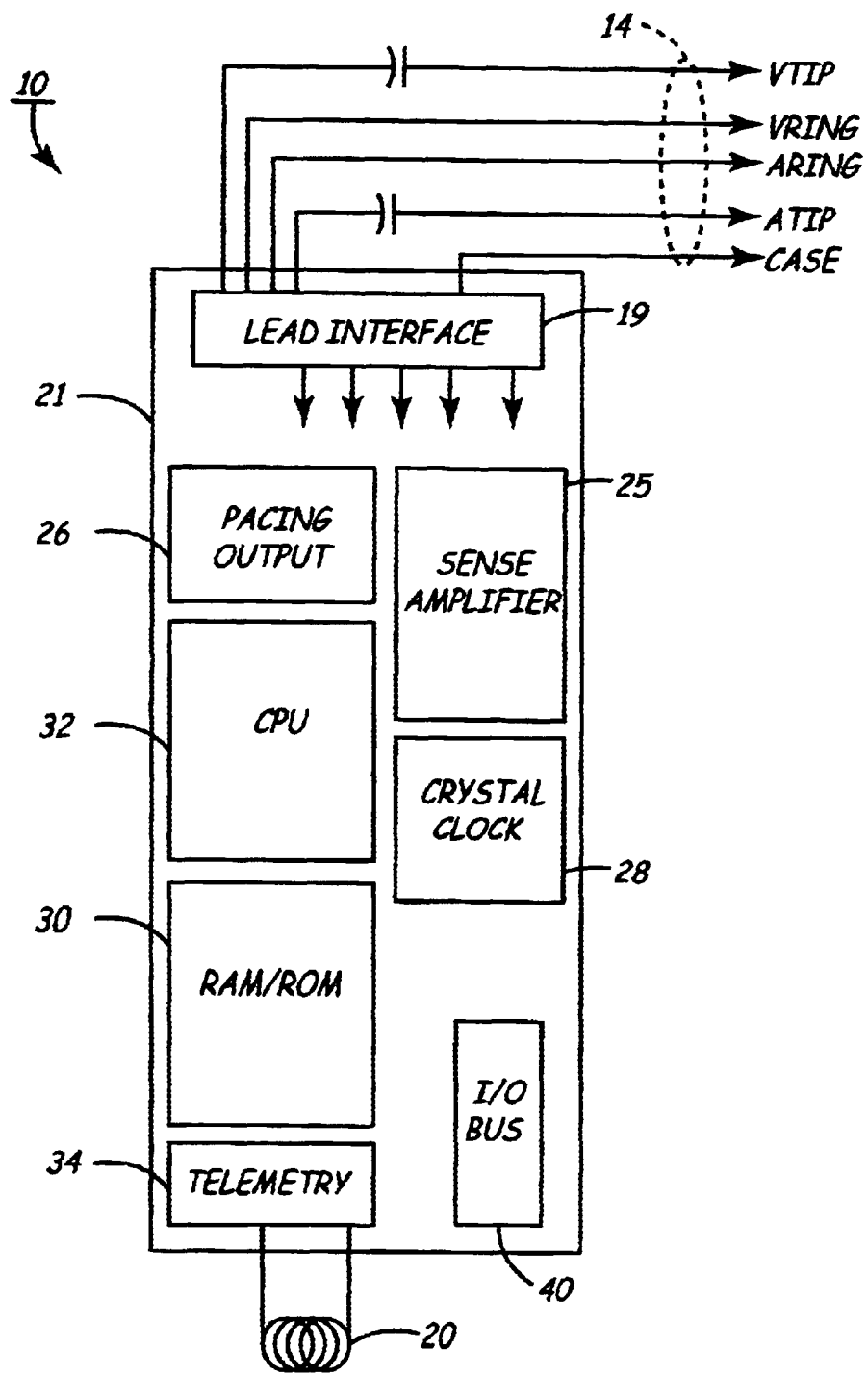
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 21 for controlling the device's pacing and sensing functions. The circuitry associated with stimulation control circuit 21 may be of conventional design, in accordance, for example, with what is disclosed U.S. Pat. No. 5,052,388 issued to Sivula et al., Method And Apparatus For Implementing Activity Sensing In A Pulse Generator. To the extent that certain components of pulse generator 10 are conventional in their design and operation, such components will not be described herein in detail, as it is believed that design and implementation of such components would be a matter of routine to those of ordinary skill in the art. For example, stimulation control circuit 21 in FIG. 3 includes sense amplifier circuitry 25, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable of communicating with external programmer/control unit 20, as described in FIG. 2 in greater detail.

Further referring to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary-connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 25 and stimulating pulse output circuit 26, in accordance with common practice, such that cardiac electrical signals may be conveyed to sensing circuitry 25, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 21 includes central processing unit 32 which may be an off-the-shelf programmable microprocessor or micro controller, but in the present invention is a custom integrated circuit. Although specific connections between CPU 32 and other components of stimulation control circuit 21 are not shown in FIG. 3, it will be apparent to those of ordinary skill in the art that CPU 32 functions to control the timed operation of stimulating pulse output circuit 26 and sense amplifier circuit 25 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator provides main timing clock signals to stimulation control circuit 21. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled Body Stimulator Output Circuit, which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 25, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 4:
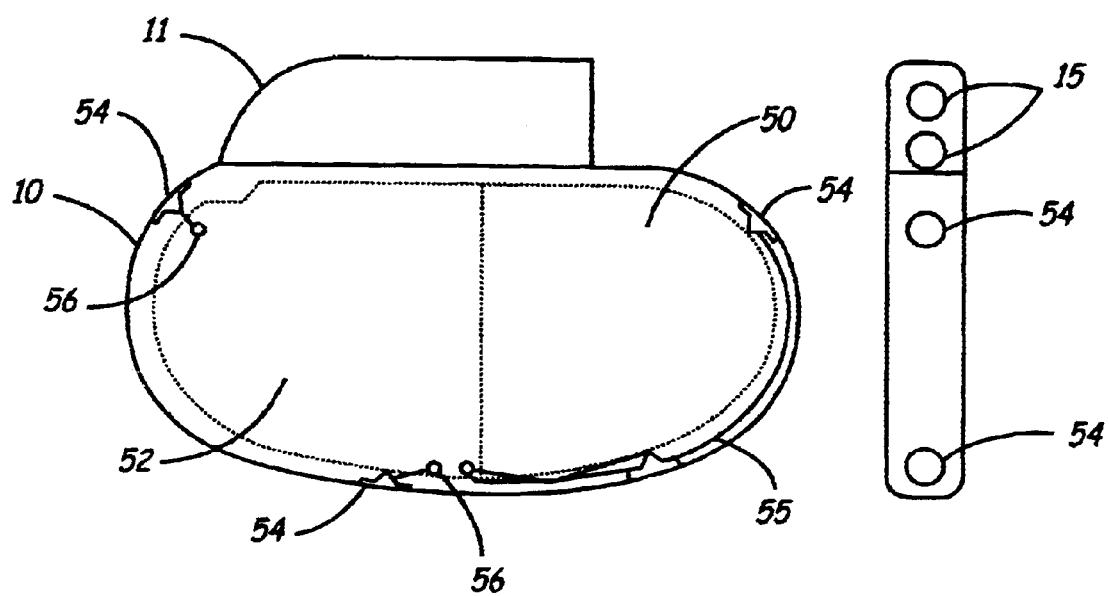
FIG. 4 is a cross sectional view of an implanted pacemaker in which the present invention may be practiced as a preferred embodiment.

FIG. 4 is a cross sectional view of implanted pacemaker 10 in which the present invention may be implemented. The major components of pacemaker 10 include a hermetic casing in which are housed electronic circuitry 52 and hermetic power source 50. Lead connector module 11 provides an enclosure in which the proximal ends of atrial and ventricular leads may be inserted into openings 15. Lead connector module 11 is connected to pacemaker casing 10 and as is well known in the art includes electrical connections (not shown) between lead connectors and hermetic feedthroughs (also not shown).

Further referring to FIG. 4, feedthrough/electrode assemblies 54 are welded into place on a generally or substantially flattened periphery of the pacemaker casing. In the preferred embodiment, the complete periphery of the pacemaker may be manufactured with a slightly flattened perspective including rounded edges to accommodate the placement of feedthrough/electrode assemblies such as those disclosed in the present invention. These feedthrough/electrode assemblies 54 are welded to pacemaker casing for integral hermiticity and connected via wire 55 through separate feedthroughs 56 to gain access to electronic circuitry 52.

FIGS. 5 represents several cross sectional views of alternative structures of the first embodiment of the present invention in combination with ECG sensing electrodes. In this embodiment, the complete assembly is quite small and designed to match with the pacemaker casing. Because of the small size of the complete assembly, the sensing electrodes must be designed and manufactured from materials capable of detecting faint/very slight cardiac depolarization waveforms, such as the P-wave.

Further, the assembly of the subcutaneous electrodes including those disclosed in FIGS. 6 through 12 hereinbelow, must be hermetic (less than $10^{-6}$ cc He/sec with $10^{-9}$ cc He/sec preferred), biocompatible, and joinable to or fully integrable with the pacemaker casing. In general, all the electrodes disclosed herein may be constructed from the following materials. The insulator may consist of glass, ceramic (direct braze), polymeric, or glass-ceramic. The ferrule may be fabricated from any suitable alloy or metal such as titanium, niobium, stainless steel, or combination of these metals and alloys. The feedthrough conductor may be made of any suitable alloy such as niobium, tantalum, platinum, or platinum-iridium. The sensing electrode may be constructed of any suitable material such as platinum, platinum black, titanium, titanium nitride, or ruthenium oxide, or combinations thereof. Electrode coating deposition methods, including sintering (powder metallurgy), sputtering, plating, CVD, PVD, or other methods, can be used to obtain large surface areas and low polarization. Ion etching, directional solidification, or other processes may be used to texture the surface to increase the surface area of the electrode and to simplify manufacturability.

Figure 5A:
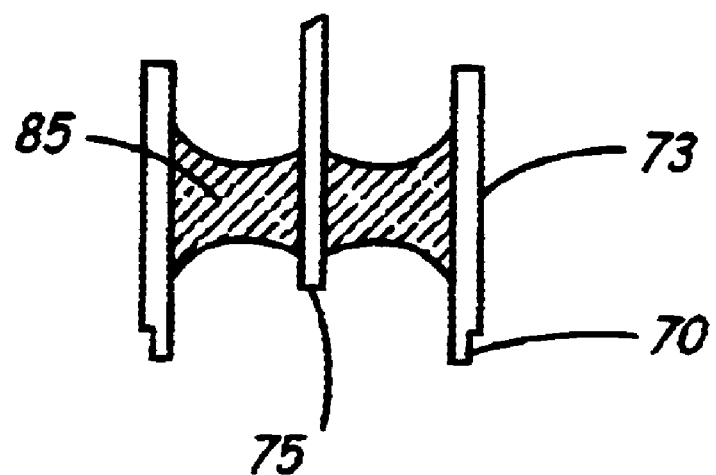
FIG. 5 provides two cross sectional views of several alternative fabrications of the first embodiment of the present invention, using simple ECG sensing electrodes.
Figure 5B:
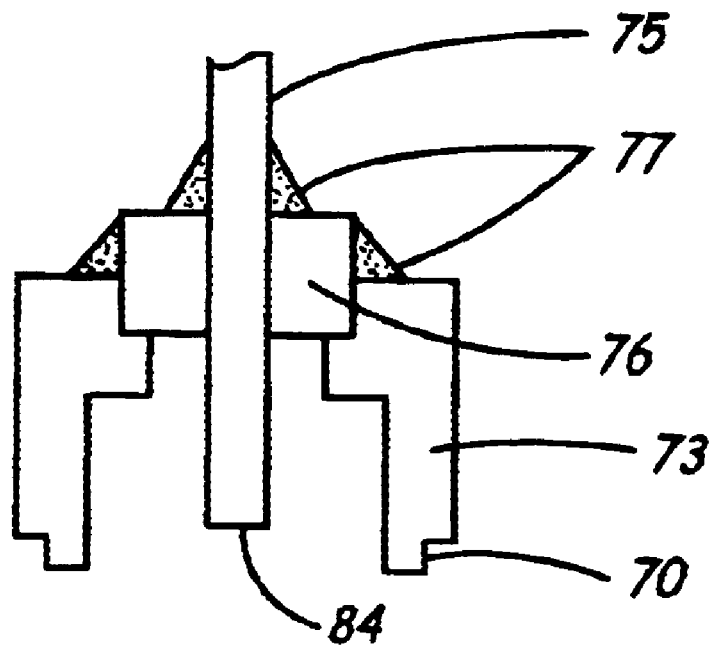

FIGS. 5A and 5B illustrate simple subcutaneous ECG electrode assemblies. FIG. 5A shows feedthrough conductor 75, mounted in ferrule 73 with optional welding notch 70 to accommodate the welding of the pacemaker casing (not shown) to ferrule 73. Glass insulator 85 joins feedthrough conductor 75 and ferrule 73. Preferably, feedthrough conductor 75 is machined to function as an ECG sensing electrode. P-8787, Thin Film Electrodes for Sensing Cardiac Depolarization Signals, by Guck et al, filed on Dec. 13, 2000, Ser. No. 09/736,046, disclosed a manufacturing process for conversion of feedthrough conductors to ECG electrodes. FIG. 5B displays brazed feedthrough 84 with a conductor 75 that is supported by insulator 76 and ferrule 73. These components are joined with gold braze 77.

The embodiments shown in FIGS. 5A and 5B disclose elegant electrode designs and a low profile. They have no appreciable protrusions and as such, lend themselves to an easier implant procedure and greater comfort for the patient.

FIG. 6 shows four views of the second embodiment of the present invention that utilizes an ECG sensing electrode with a large surface area. FIG. 6A is a cross sectional view, 6B a top view, 6C a perspective view, and 6D a cross sectional view all which represent, inter alia, a glass insulator within a modified ferrule casing.

Referring to FIG. 6A, a cross-sectional view of feedthrough conductor 75 terminating in a substantially flat-ended electrode 74 is shown. Electrode 74 is recessed within ferrule 73 that is welded to the pacemaker casing at optional welding notch 70. Thus, the complete assembly has no components that protrude above or outside of the pacemaker's casing. Feedthrough conductor 75 fits through opening in insulator 76 to which it is joined by braze 77. Insulator 76 maintains electrical isolation of the ECG signal as it circuits from sensing electrode 74 through feedthrough conductor 75 that is electrically connected to SEA circuitry within pacemaker 10. Braze 77 serves to hermetically seal the assembly and prevent the intrusion of body fluid that fills the cavity around electrode 74.

In this embodiment, the increased surface area of ECG sensing electrode 74 is one of the significant features of the invention. The geometric surface area is increased to improve detection of cardiac waveforms that have lesser amplitudes, for example, atrial fibrillation waves. In addition, increasing the geometric surface area may attenuate polarization effects at or around the ECG sensing electrode. Both features help to ensure the appropriate detection of ECG waveforms. The structure enables adequate detection, and transmission of cardiac depolarization signals. In an alternate embodiment, electrode coatings may be used to obtain larger surface areas and effect low polarization. Coating deposition methods may include sintering (powder metallurgy), sputtering, plating, CVD, PVD, or other methods. In addition, ion etching, directional solidification, or other processes may be used to texture the surface to increase the surface area of the electrode and to simplify manufacturability.

Sensing electrode 74 may be integral and homogenous with feedthrough conductor 75 and established via deposition methods such as sintering, sputtering, plating, etc. Alternatively, sensing electrode 74 may be subsequently attached to the feedthrough conductor via shape memory alloys, welding, brazing, compression interference joints, etc.

FIG. 6D shows a cross sectional view of the embodiment in which the same feedthrough conductor 75 and sensing electrode 74 are used, with the exception that glass 85 is used to 1) join the feedthrough conductor/electrode with the ferrule, 2) electrically insulate so as to maintain signal integrity, and 3) hermetically seal the assembly.

FIG. 7 shows four views of a third embodiment of the present invention that utilizes an ECG sensing electrode with a low profile and a filter(i.e/, capacitor).

FIG. 7A shows the addition of a multi-layer ceramic capacitor 71 that serves to filter electromagnetic interference to improve the detected signal prior to passing the signal on to the pacemaker circuitry. The feedthrough conductor and feedthrough ferrule are electrically joined to the capacitor. Capacitor 71 can be placed in the assembly and stabilized using non-conductive epoxy 79. Conductive epoxy 78 may be used to couple capacitor 71 with feedthrough conductor 75. Note also that in FIG. 7D, the filter capacitor 71 is used with glass insulator 85.

FIG. 8 shows four views of yet another embodiment of the present invention that utilizes both an ECG sensing electrode with a high surface area and a capacitor. In FIG. 8A, ECG sensing electrode 74 is implemented in a manner similar to that disclosed in conjunction with FIG. 6, the second embodiment. The reasons for using a sensing electrode with a high surface area are the same as those cited in FIG. 6.

Figure 9B:
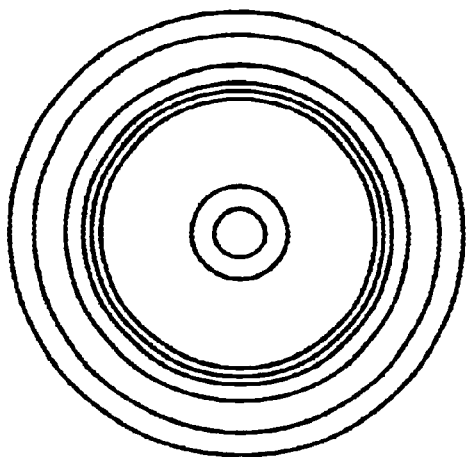
FIG. 9 shows three views of how the third and fourth embodiments (FIGS. 7 and 8) of the present invention may be assembled with a polyimide disk to render the assembly as leak testable.
Figure 9C:
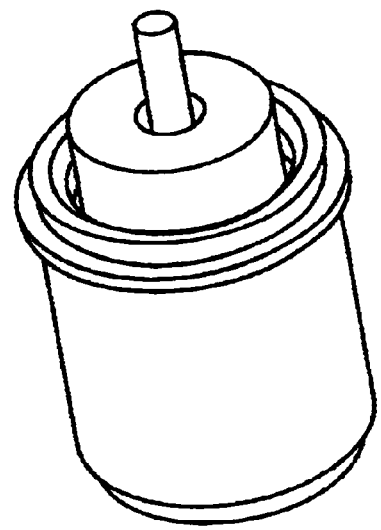
Figure 9A:
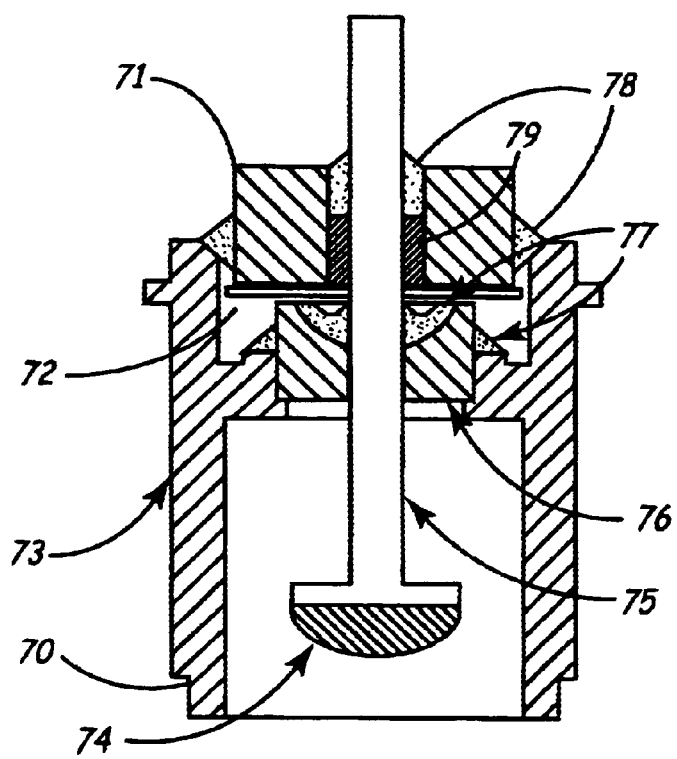

FIG. 9 shows three views of how the third and fourth embodiments (FIGS. 7 and 8) of the present invention may be assembled with a polyimide disk to render the assembly leak testable. This figure focuses on the important element of testing for hermeticity, that is, determining whether the assembly may be tested for leaks. The addition of polyimide disk 72 immediately below capacitor 71 accomplishes this purpose. For further description of a leak testable feedthrough, reference is made to P-8990, Leak Testable Capacitive Filtered Feedthrough for an Implantable Medical Device, by Fraley et al, filed Oct. 25, 2000, Ser. No. 09/696,601, that is incorporated herein by reference in its totality. As with the embodiments disclosed hereinabove, the same element could be added to an assembly using glass as an insulator (not shown).

Figure 10:
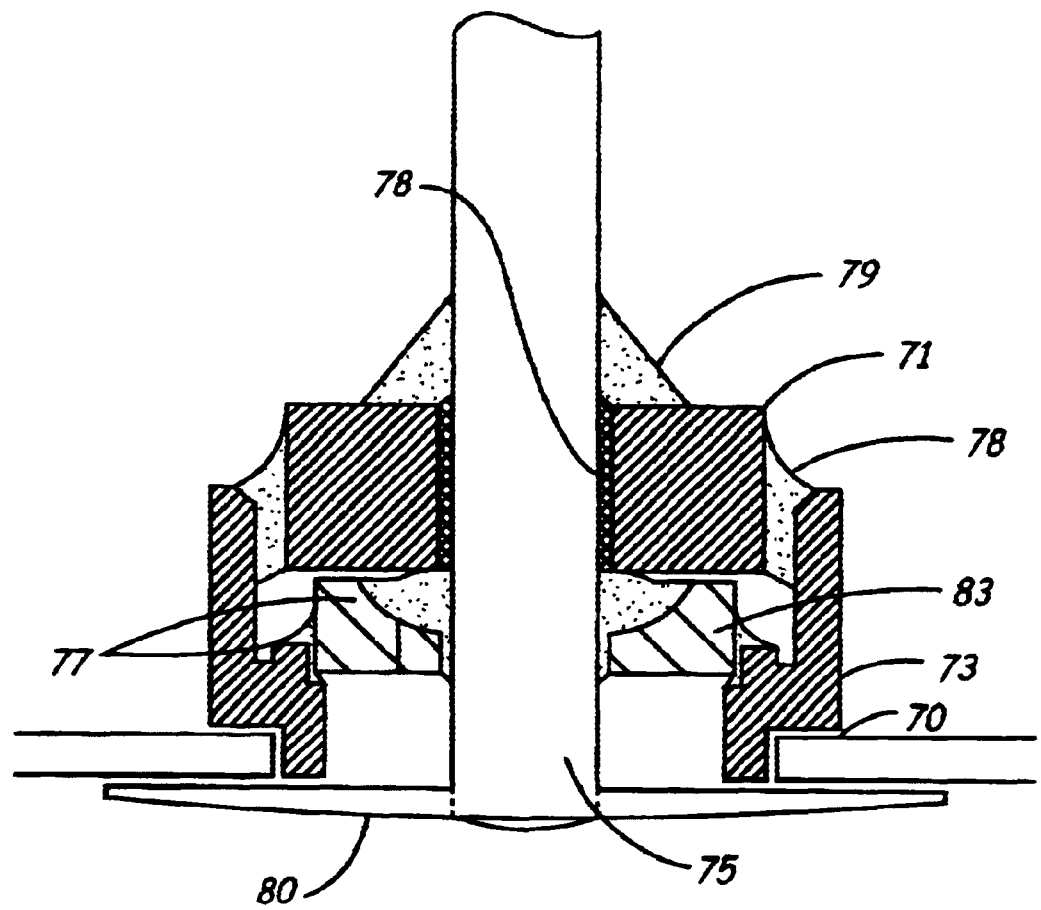
FIG. 10 shows a cross, sectional view of the present invention with a low-profile disk electrode.

FIG. 10 shows a cross sectional view of the present invention with a low-profile/high surface area disk electrode 80. Specifically, electrode 80 may be implemented in the embodiments disclosed in FIGS. 6 and 8 to further increase the surface area of the ECG sensing electrode. The electrodes are attached to the feedthrough conductor after welding the feedthrough to the shield. Electrode attachment may be performed by laser weld, resistance spot weld, mechanical interference, or other equivalent methods.

FIG. 11 is a representation of various electrode types that may be used with the assemblies shown in the embodiments disclosed hereinabove. FIG. 11A is a standard, substantially flat headed, feedthrough conductor to which is attached sensing electrode 86 (as was shown in FIG. 6). Alternative types of electrodes may be used, as shown in FIGS. 11B and 11C. Feedthrough conductor 75 may be modified to contain a platinum powder chamber 67. Electrode 75 in FIG. 11B is coated and sintered with Pt powder 68. Electrode 75 in FIG. 11C is coated and sintered with Pt powder 68 and with Pt black 69. In accordance with the present invention, any combination of sintered Pt 68 and Pt black 69 may be used. All electrodes may include a steroid plug 82 as shown in FIG 11D. FIGS. 11E and 11F represent stages of manufacture in accordance with the present invention. Specifically, a shown in FIG. 11F, electrode 75 protrudes through electrode disk 80. The protrusion is preferably laser welded or mechanically formed to have a compliant contour as shown in FIG 11E. The feedthrough conductor fits through the low-profile electrode disk 80. As shown in FIG. 11F by dotted lines, the feedthrough conductor protrudes through the disk and is welded to attach electrode 75 to feedthrough conductor as shown in FIG. 11E.

Figures 12A, 12B:
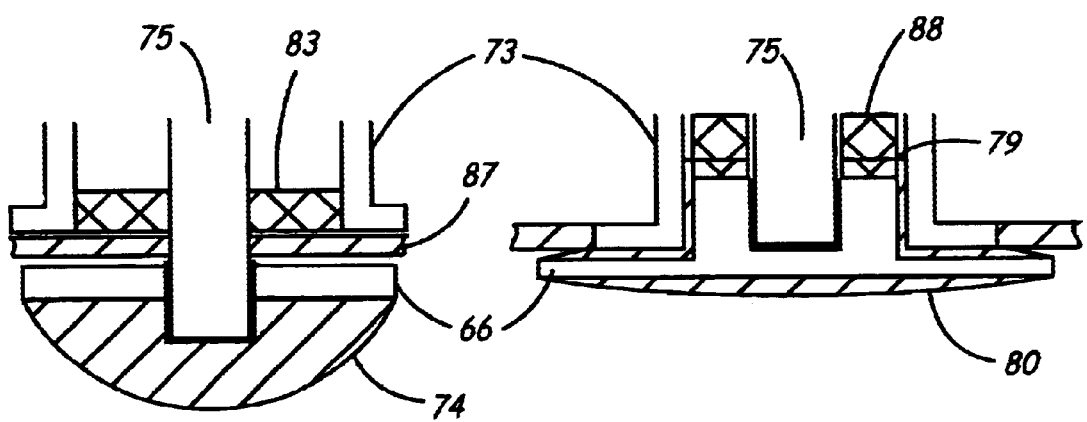
FIG. 12A and FIG. 12B show a cross sectional view of electrodes attached to a feedthrough conductor through the use of a shape memory alloy.

FIGS. 12A and 12B are examples of assemblies that make use of shape memory alloy 66 to allow easier and less costly fabrication. FIG. 12A represents the implementation of a ceramic or glass insulator 83, with an insulator of another material 87 to electrically isolate sensing electrode 74 from ferrule 73 and pacemaker casing (not shown). The electrode in FIG. 12B, is an alternate embodiment using epoxy backfill 79 and insulator 88 to electrically isolate the low-profile sensing electrode 80 from ferrule 73 and pacemaker casing.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. An IMD including at least one electrode incorporated into a feedthrough for electrical coupling with a circuit of the IMD to detect physiological signals, the electrode in combination with the feedthrough comprising:

the electrode disposed in a ferrule conforming to a periphery of IMD;

insulator means between said electrode and said ferrule; and electrical coupling means between said electrode and said circuit.

2. The IMD of claim 1 wherein said electrode includes a substantially flat end integrated with a generally flattened exposed periphery of the IMD forming a hermetic seal therewith.

3. The IMD of claim 2 wherein a plurality of electrodes are distributed around said exposed periphery of the IMD forming an array.

4. The IMD of claim 2 wherein a braze connects said electrode, said ferrule and said insulator to form said hermetic seal.

5. A sensing electrode system wherein one or more electrodes are disposed around the perimetric periphery of an implantable medical device (IMD), the sensing electrode system comprising:

a first end integrated with a feedthrough conductor;

insulator means having an opening to encase a segment of said first end;

braze means to hermetically seal and integrally connect said first end with said insulator and said insulator with a ferrule; and a second end forming a large surface area extending through said ferrule;

said first end being electrically coupled to a circuit in the IMD, said second end providing sensing to process physiologic signals obtained via said large surface area.

6. The system of claim 5 wherein a plurality of electrodes are distributed at perimetric periphery of the IMD with said large surface area of said second end being in planar conformity with the periphery of the IMD.

7. The system of claim 5 wherein said insulation means and said braze means are jointly replaced by a glass structure.

8. The system of claim 5 wherein said second end extends into bodily fluids of the patient in whom the IMD is implanted.

9. An implantable medical device (IMD) having a hermetically sealed housing having a housing outer wall exposed to the body and a housing inner wall enclosing sensing circuitry within said housing for processing electrical signals of the body detected between at least two sense electrodes supported by the housing, wherein;

at least one sense electrode comprises a electrical feedthrough mounted to extend between said housing first side and said housing second side, said feedthrough comprising a ferrule having an inner ferrule surface extending between a ferrule first end and a ferrule second end, an electrically conductive feedthrough pin extending between a feedthrough pin first end and a feedthrough pin second end, and an electrical insulator extending between said feedthrough pin and said ferrule inner wall and supporting said feedthrough pin; and further comprising:

means for mounting said ferrule wall first end to extend said feedthrough pin through said housing to expose said feedthrough pin first end to the body and to hermetically enclose said feedthrough pin second end within said housing; and means for electrically coupling said feedthrough pin second end with said sensing circuitry thereby enabling said feedthrough pin first end to function as a first sense electrode operable in conjunction with a second sense electrode coupled with the sensing circuitry to enable sensing of electrical signals of the body.

10. The IMD of claim 9, wherein each feedthrough:

the ferrule first end is mounted flush with the outer housing wall and the ferrule second end extends within said housing; and said insulator is mounted to extend between said ferrule inner wall within said housing and said feedthrough pin and supports the feedthrough pin first end recessed into the ferrule away from the ferrule first end.

11. The IMD of claim 10, wherein in each feedthrough:

the feedthrough pin has a pin diameter extending through said insulator; and the feedthrough pin has an enlarged electrode diameter at the feedthrough pin first end providing an enlarged electrode surface area.

12. The IMD of claim 10, wherein the feedthrough pin first end is subjected to a surface treatment selected from the group consisting of sintering, sputtering, plating, CVD and PVD.

13. The IMD of claim 10, wherein the feedthrough further comprises a capacitive filter mounted between said ferrule and said feedthrough pin.

14. The IMD of claim 10, wherein each feedthrough:

the feedthrough ferrule is cylindrical in shape between the ferrule first end and the ferrule second end and has a ferrule diameter;

the feedthrough pin has an enlarged electrode diameter less than the ferrule diameter at the feedthrough pin first end forming an enlarged electrode surface area.

15. The IMD of claim 14, wherein the enlarged electrode surface area is enhanced by a surface treatment selected from the group consisting of sintering, sputtering, plating, CVD and PVD.

16. The IMD of claim 14, wherein the feedthrough further comprises a discoidal capacitive filter mounted between said ferrule inner wall and said feedthrough pin.

17. The IMD of claim 9, wherein each feedthrough:

the ferrule first end is mount flush with the outer housing wall and the ferrule second end extends within said housing; and said insulator is mounted to extend between said ferrule inner wall within said housing and said feedthrough pin and supports the feedthrough pin first end extending past the ferrule first end and outward of the housing exposed wall.

18. The IMD of claim 17, wherein each feedthrough:

the feedthrough pin has a [in] diameter extending through said insulator; and the feedthrough pin has an enlarged electrode having an enlarged electrode diameter at the feedthrough pin first end providing an enlarged electrode surface area extending outward over the housing outer wall.

19. The IMD of claim 18, wherein the feedthrough pin first end is subjected to a surface treatment selected from the group consisting of sintering, sputtering, plating, CVD and PVD.

20. The IMD of claim 18, wherein the feedthrough further comprises a capacitive filter mounted between said ferrule and said feedthrough pin.

21. The IMD of claim 18, further comprising unseating means separating the enlarged electrode extending outward over the housing outer wall from the ferrule first end and the housing outer wall.

22. The IMD of claim 18, wherein each feedthrough:

the feedthrough ferrule is cylindrical in shape between the ferrule first end and the ferrule second end and has a ferrule diameter;

the feedthrough pin has a pin diameter extending through said insulator; and the feedthrough pin has an enlarged electrode having electrode diameter exceeding the ferrule diameter at the feedthrough pin first end forming an enlarged electrode surface area extending outward over the housing outer wall.

23. The IMD of claim 22, further comprising insulating means for electrically insulating the enlarged electrode extending outward over the housing outer wall from the ferrule first end and the housing outer wall.

24. The IMD of claim 22, wherein the enlarged electrode surface area is enhanced by a surface treatment selected from the group consisting of sintering, sputtering, plating, CVD and PVD.

25. The IMD of claim 22, wherein the feedthrough further comprises a discoidal capacitive filter mounted between said ferrule inner wall and said feedthrough pin.

26. The IMD of claim 9, wherein the feedthrough pin first end is subjected to a surface treatment.

27. The IMD of claim 9 wherein, wherein a plurality of sense electrodes are each formed of a like plurality of said feedthroughs each electrically connected with said sensing circuitry to process a plurality of electrical signals detected from selected pairs of feedthrough pin first ends.

28. The IMD of claim 9 wherein:

a plurality of sense electrodes are each formed of a like plurality of said feedthroughs each electrically connected with said sending circuitry to process a plurality of electrical signals detected from selected pairs of feedthrough pin first ends; and said housing comprises a pair of opposed major housing walls joined at their peripheries by a perimeter, and each ferrule of said plurality of feedthroughs is attached to an opening through said perimeter of said housing.

29. The IMD of claim 9, wherein each feedthrough:

the feedthrough pin has a pin diameter extending through said insulator;

the feedthrough pin has an enlarged electrode diameter at the feedthrough pin first end providing an enlarged electrode surface area.

30. The IMD of claim 9, wherein said housing comprises a pair of opposed major housing walls joined at their peripheries by a perimeter, and the ferrule of said feedthrough is attached to an opening through said perimeter of said housing.

31. The IMD of claim 9, wherein the feedthrough pin first end is subjected to a surface treatment selected from the group consisting of sintering, sputtering, plating, CVD and PVD.

32. The IMD of claim 9, wherein each feedthrough further comprises a capacitive filter mounted between said ferrule and said feedthrough pin.

33. The IMD of claim 9, wherein the insulator further comprises an electrically insulating glass extending between a portion of the length of the feedthrough pin and at least a portion of the inner ferrule surface and adhered thereto to form a hermetic seal of the pin to the ferrule.

34. The IMD of claim 9, wherein the insulator further comprises an electrically insulating ceramic insulator extending between a portion of the length of the feedthrough pin and adhered thereto by a braze and to at least a portion of the inner ferrule surface and adhered thereto by a braze to form a hermetic seal of the pin to the ferrule.

35. The IMD of claim 9, wherein the insulator extends between a first portion of the length of the feedthrough pin and a first portion of the inner ferrule surface, and the feedthrough further comprises:

a capacitive filter mounted between a second portion of the inner ferrule surface and the feedthrough pin; and a polyamide disk between the capacitive filter and the insulator to facilitate hermetic leak testing of the insulator.

36. The IMD of claim 9 wherein a shape memory alloy is implemented to provide ease of assembly between the feedthrough and the sensing electrode.

37. The IMD of claim 36 wherein said shape memory alloy is structured to support the feedthrough and the sensing electrode forming a compact assembly thereof.

38. The IMD of claim 9 wherein said feedthrough and said electrode are integrally attached using one of a weld and mechanical forming process.

\* \* \* \* \*